United States Patent [19]

Narisada et al.

[11] 4,376,770

[45] Mar. 15, 1983

[54] CEPHALOSPORIN ANALOGS FOR ORAL USE

[75] Inventors: Masayuki Narisada, Ibaraki; Tetso Okada, Sakai; Tadashi Yoshida, Osaka; Shinzo Matsuura, Itami, all of Japan

[73] Assignee: Shionogi & Co., Ltd., Osaka, Japan

[21] Appl. No.: 285,876

[22] Filed: Jul. 23, 1981

[30] Foreign Application Priority Data

Jul. 23, 1980 [JP] Japan .................. 55-101779

[51] Int. Cl.³ .................. A61K 31/535; C07D 498/04
[52] U.S. Cl. .................. 424/248.51; 424/248.52; 544/90
[58] Field of Search .................. 544/90; 424/248.51, 424/248.52

[56] References Cited

FOREIGN PATENT DOCUMENTS

53/84987 7/1978 Japan .................. 546/90
53/149991 12/1978 Japan .................. 546/90

Primary Examiner—Robert T. Bond

Attorney, Agent, or Firm—Wenderoth, Lind & Ponack

[57] ABSTRACT

7β-(2-Cyano-aliphatic acylamino)-7α-methoxy-3-heterocyclic thiomethyl-1-dethia-1-oxa-3-cephem-4-carboxylic acids and salts or pharmacologically acceptable esters generically represented by the following formula are potent antibacterials and esters are prospective oral drugs:

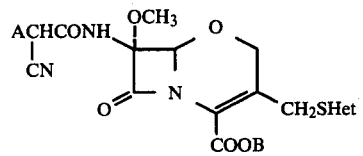

(wherein
A is a lower alkyl, lower alkenyl or lower alkynyl group;
B is a hydrogen atom, salt forming atom, salt forming group or physiologically hydrolyzable ester group; and
Het is a heterocyclic group).

20 Claims, No Drawings

CEPHALOSPORIN ANALOGS FOR ORAL USE

This invention relates to an aliphatic acylaminooxacephalosporin compound represented by the following formula (I):

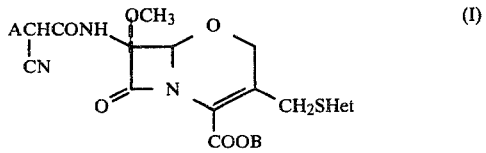

(wherein

A is a lower alkyl, lower alkenyl or lower alkynyl;

B is a hydrogen atom, salt forming atom or group or biochemically hydrolyzable ester group or carboxy protecting group conventional in the art; and Het is a heterocyclic group)

More specifically, this invention relates to a biochemically hydrolyzable ester included in the above aliphatic acylaminooxacephalosporin compound (I).

Up to now, a number of oxacephalosporins have been synthesized. However, none of them was suitable for oral use. Then, the inventors looked for a compound capable of being administered orally and have found the esters represented by above formula (I) to show practical antibacterial effect.

In above formula (I), the lower alkyl represented by A can preferably be a methyl, ethyl, propyl, isopropyl, pentyl, cyclopentyl, neopentyl, hexyl, octyl or isooctyl, especially $C_1$ to $C_8$-, particularly $C_1$ to $C_4$-alkyl group.

The lower alkenyl group represented by A can preferably be a vinyl, allyl, butenyl or pentadienyl, especially $C_2$ to $C_8$-, particularly $C_3$ to $C_4$-alkenyl.

The lower alkynyl group represented by A can preferably be ethynyl, propargyl or pentynyl, especially $C_2$ to $C_8$-, particularly $C_3$ to $C_4$-alkynyl.

As stated above, the A group may have a straight, branched or cyclic nucleus. Preferable A group for oral absorption has $C_1$ to $C_3$- and for antibacterial activity has a straight $C_1$ to $C_4$-chain. Those having A as hydrogen are not practical antibacterials.

Biochemically hydrolyzable ester $B^1$ included within the scope of the definition of B can preferably be the acetoxymethyl ester, acetoxy ethyl ester, propionyloxyethyl ester, butyryloxyethyl ester, pivaloyloxymethyl ester, heptanoyloxypropyl ester group or like straight or branched chain $C_2$ to $C_8$-alkanoyloxy-$C_1$ to $C_5$-alkyl ester group; methoxycarbonyloxyethyl ester, ethoxycarbonyloxyethyl ester, propoxycarbonyloxypropyl ester, butoxycarbonyloxyethyl ester, or like 1-acyloxyalkyl ester group, especially $C_1$ to $C_5$-alkoxycarbonyloxy-$C_1$ to $C_4$-alkyl ester group; cyclic 1-acyloxyaralkyl ester group e.g. phthalidyl ester group; or other conventional ester forming group hydrolyzable physiologically or by cell enzyme. One type of especially preferable ester group is that difficultly hydrolyzed in the digestive organs and absorbed to elevate blood level up to an antibacterially effective level, and that hydrolyzed until attacking bacteria.

When the B group in the formula (I) is a hydrogen atom, light metal atom or salt forming group, the resulting acid and salts are parenteral antibacterials and at the same time, intermediates for synthesizing esterified Compound (I). Light metal atom can be lithium, sodium, potassium, magnesium, calcium, aluminum or like atoms and representative salt forming group can be tertiary ammonium, quaternary ammonium or mono or bicyclic aromatic base group. Preferable among these are pharmacologically acceptable salts or that having a base part sufficiently strong for the esterification.

Heterocyclic groups represented by Het are monocyclic and may contain 1 to 4 heteroatoms selected from nitrogen, sulfur and oxygen. These can optionally be substituted by alkyl, haloalkyl, hydroxyalkyl, alkoxyalkyl, carboxyalkyl, conventionally protected carboxyalkyl, carbamoylalkyl, N-alkylcarbamoylalkyl, dialkylaminoalkyl, sulfamoylalkyl, N-alkylsulfamoylalkyl or other $C_1$ to $C_6$-substituent or hydroxy, oxo or halogen. Carboxy protection may be mono- or dicyclic aralkyl or a kind of the $B^1$ group. Especially preferable are triazolyl, tetrazolyl, thiadiazolyl oxadiazolyl, thiazolyl, oxazolyl, isoxazolyl, triazinyl, pyridyl, pyrimidyl or like groups. As stated above, these may optionally be substituted by alkyl e.g. methyl, ethyl, isobutyl or other $C_1$ to $C_5$-alkyl; substituted alkyl e.g. hydroxymethyl, carboxymethyl, dimethylaminoethyl or other $C_1$ to $C_5$ substituted alkyl; oxo; hydroxy; halogen or like substituents.

The 7α-methoxy group prevents loss of activity due to some β-lactamase. The cyano group in the side chain activates the effect against gram-negative bacteria. The A group enables enteral administration.

7β-Cyanoacetamidocephalosporanic acid disclosed in South African Pat. No. 6950/1965 has been in the drug market, but its pivaloyloxymethyl ester does not show oral absorption sufficient as clinical drugs.

7β-Cyanoacetamido-1-dethia-1-oxacephalosporanic acid suggested in Japanese Published Patent Application (Kokai) 49-133594 is a weak antibacterial even when 7α-methoxy is added it does not prove of practical value as an antibacterial.

Surprisingly, the introduction of an aliphatic group into the α-position of the cyanoacetamido side chain of the compounds of the prior yields the said Compound (I) resulting in exceeding antibacterial activity coupled with enteric absorption to show prospective medical availability as oral drugs.

The said Compounds (I) are strong antibacterials against *Staphylococcus aureus, Streptococcus haemophylis, Streptococcus pneumonia* or other gram-positive bacteria and against *Escherichia coli* or those of genera Klebsiella, Proteus of indol-positive and negative strains, Serratia or like gram-negative strains. They are effective also against clinical anaerobic bacteria.

Outstanding clinical effects of the Compounds (I) can be observed when they are used to treat or prevent e.g. urinary tract infection, respiratory tract infection, dermatitis, abdominal infection, pyelitis, osteomyelitis, or meningitis caused by sensitive bacteria at a daily oral dose of 2 to 8 grams. The Compound (I) can be used by other parenteral route e.g. intravenous or intramuscular injection or rectal application. The free acid or its salt of Compounds (I) can be used for parenteral administration or for synthesizing the ester Compounds (I). The parenteral case requires generally a daily dose of e.g. 0.1 to 3 g. for injection and much lower dose for topical application.

The Compounds (I) can be formulated to make oral preparations combined with a bulking agent, binding agent, disgrating agent, fillers, lubricant, coating agent, pH-controlling agent, solvent or the like conventional additive to make tablets, capsules, granules or other oral drugs, or parenteral preparation e.g. vials, ampoules, suppositories, or dermatological agents.

Compounds (I) can be synthesized by introducing the B group, side chain acyl group or cyano group, all applying conventional procedures in the art.

(a) Introduction of the $B^1$ group:

Compounds (I) can be prepared by reacting the corresponding carboxylic acid or its salt (II) and an esterifying reagent (III) for introducing the $B^1$ group.

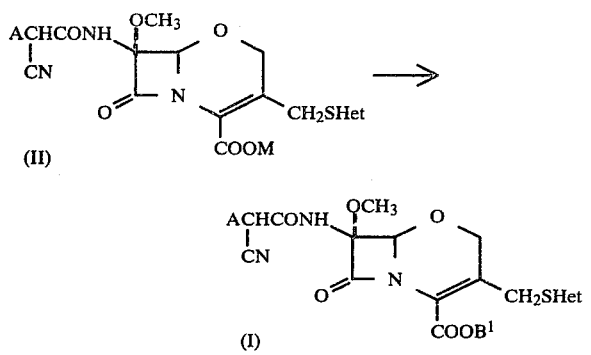

(wherein

A and Het are as defined above;

$B^1$ is a biochemically hydrolyzable ester group;

M is a hydrogen atom, salt-forming atom or salt forming group; and

X is a leaving group)

The salt forming atom shown by M can preferably be e.g. a lithium, sodium, potassium, magnesium, calcium, aluminum or like light metal atom and the salt forming group shown by M can be e.g. aliphatic or aromatic lower tertiary ammonium, quaternary ammonium, mono- or dicyclic aromatic base, etc.

The leaving group X can preferably be halogen, sulfonyloxy, lower alkanoyloxy, hydroxy or the like group conventional for acylation in the art.

The reaction is carried out as a solution in an industrially available inert polar solvent for dissolving the carboxylic acid (II) or its salt such as nitrile, amide, sulfoxide, ketone, ester, ether or like solvent especially acetonitrile, N,N-dimethylformamide, N,N-dimethylacetamide, formamide, dimethyl sulfoxide, acetone, ethyl acetate, diglyme or dioxane. Reaction temperature usually is between −20° C. to 100° C. If required, a condensing agent, accelerating agent or like is added to promote the esterification.

Preferably, 1 to 2 equivalents of the esterifying reagent (III) is used for the carboxylic acid salt (II) and allowed to react at 0° C. to 35° C. The carboxylic acid (II) is converted to its salt and then treated with the acylating reagent (III) as described above. The acylation completes usually in from 1 to 3 hours if treated as above to afford the objective compounds in 50% to 90% yield. This is specific for introducing the $B^1$ group but other equivalent and conventional conditions may be available for the same purpose.

(b) Introduction of the side chain:

Compounds (I) can be produced by amidating an amino compound (IV) with an acylating reagent for introducing the α-cyanoaliphatic acyl group.

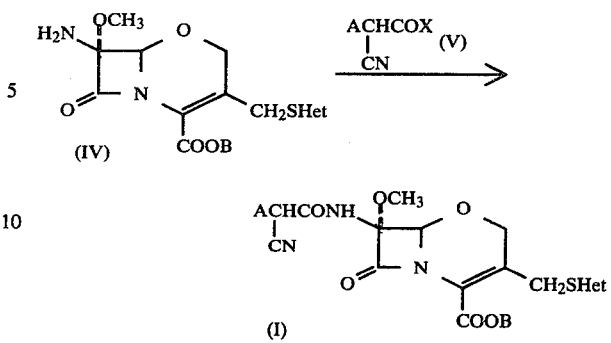

(wherein A, B, Het and X are as defined before)

The amino compound (IV) can be produced e.g. by a method suggested in Japanese Published Patent Application (Kokai) 49-133594.

This step may be carried out using a free acid (Compound (V) with X as OH) in the presence of e.g. N,N′-dicyclohexylcarbodiimide, 1-hydroxybenzotriazole or 1-ethoxycarbonyl-2-ethoxy-1,2-dihydroquinoline, carbonyldiimidazole or other condensing reagent.

Alternatively, acid halides, symmetric acid anhydride or mixed acid anhydride (Compound (V) with X as halogen or acyloxy) can be used in the presence of an acid scavenger e.g. an aromatic base (pyridine, collidine, quinoline, etc.) or inorganic base e.g. sodium carbonate, potassium hydrogen carbonate, trialkylamine, oxirane or like reagents.

Further, other types of acylating reagents known in the art, e.g. reactive esters and reactive amides are available as the reagent (V) for introducing the side chain according to conventional methods. Preactivation e.g. silylation or phosphinylation of the amino group or pretreatment to form some acylate, imidate or Schiff base prior to the treatment with said acylating reagent, enzymatic acylation with an acylating reagent (V) having lower alkoxy as X in the presence of a bacterial or fungal amidase in an aqueous medium; or other conventional amidation in the art can also be available as equivalent alternatives.

These reactions are carried out at a temperature of −50° C. to 100° C. in an inert solvent e.g. aromatic hydrocarbon, halohydrocarbon, ester, ether or ketone solvent by conventional ways. Acid halides may be used in an aqueous solvent in the presence of a base.

Preferably, 1 to 2 mole equivalents of the acylating reagent (V) may be used for the amino compound (IV) and let react at −20° C. to 30° C. for 1/6 to 2 hours to give Compound (I) in 80 to 90% yield.

(c) Introduction of the cyano group:

Compounds (VI) having an aliphatic carboxylic amido side chain having a functional group replaceable with a cyano group can afford the objective Compound (I) as a result of the substitution with a cyano group, according to the following reaction scheme.

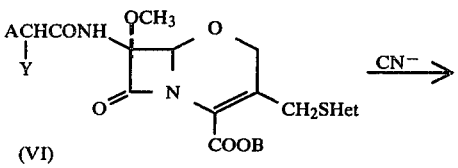

-continued

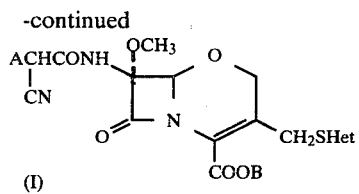

(wherein

A, B and Het are as defined before; and

Y is a functional group changeable into cyano)

Compound (IV) can be prepared e.g. by the acylation of Compound (IV). The Y group convertible into cyano can be halogen, sulfonyloxy, carbamoyl or the like. The conversion can be effected, when Y is halogen or sulfonyloxy, with alkali metal cyanide or alkaline earth metal cyanide in a said polar solvent at room temperature or when Y is carbamoyl, with a dehydrating agent e.g. phosphorus pentachloride in the presence of an acid scavenger preferably in an aprotic solvent.

Compounds (I) can alternatively be prepared by such conventional routes as methoxylation at the 7α-position e.g. by the action of lithium methoxide and tertiary butyl hypohalite at $-40°$ C. and then treating with sodium hydrogen sulfite; alkylation at the 2-position in the 7β-side chain of the corresponding 7β-cyanoacetamido-7α-methoxy-3-heterocyclic thiomethyl-1-dethia-1-oxa-3-cephem-4-carboxylic acid esters with e.g. alkyl halide or alkenyl halide in acetone containing potassium carbonate at room temperature or by the action of lithium N,N-diisopropylamide and alkyl halide in tetrahydrofuran or dimethylformamide at $-20°$ C.; substitution of e.g. halogen at the 3-position of the corresponding 3-halomethyl-3-halo-1-dethia-1-oxacepham compound in dichloromethane and water in the presence of tetra-N-butylammonium bromide and sodium hydrogen carbonate and HetSH at room temperature; the salt formation by e.g. neutralizing Compound (I) as carboxylic acid and alkali metal alkanoate in a polar solvent e.g. alcohol or methylethyl ketone; or the like methods.

Above reactions can be done at $-50°$ C. to $100°$ C. and can be checked by e.g. chromatography. The products thus prepared are isolated by extraction, washing, drying, concentration, crystallization or other conventional methods and can be purified by e.g. absorption, chromatography, recrystallization or other conventional methods.

Following Examples illustrate the present invention. The products are epimeric mixture in terms of α-asymmetric carbon in the side chain. Under careful chromatographic separation from, the epimers can be separated each other as R- and S-epimers.

Throughout the Examples, NMR signals are represented by showing chemical shift in numeral in ppm, type of signals in alphabet character, Coupling constant in parentheses if any, and integral of signals to show number of hydrogens. Abbreviations for the groups in the following reaction scheme include the followings: Ph is phenyl, Tetr is 1-methyl-5-tetrazolyl, Tdz is 1,3,4-thiadiazolyl, TdzMe is 2-methyl-1,3,4-thiadiazol-5-yl, POM is pivaloyloxymethyl, and ECE is 1-(ethoxycarbonyloxy)ethyl. Other abbreviations have conventional meanings.

PREPARATION 1.

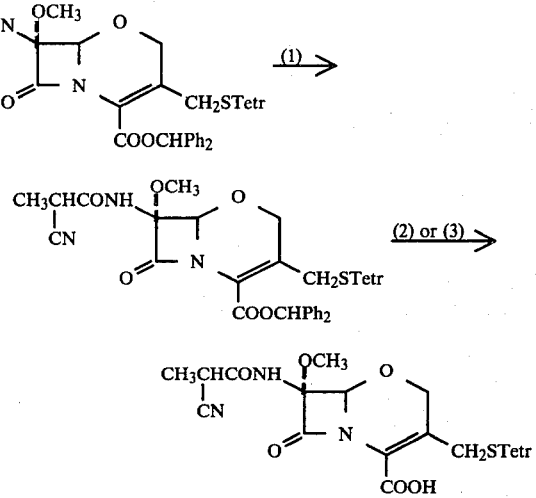

(a) To a suspension of 7β-amino-7 α-methoxy-3-(1-methyl-5-tetrazolyl)thiomethyl-1-dethia-1-oxa-3-cephem-4-carboxylic acid diphenylmethyl ester (76.2 g) in dichloromethane (12 parts by weight) cooled at $-20°$ C. are added α-cyanopropionic acid (1.5 equivalents), pyridine (4 equivalents) and phosphorus oxychloride (1.5 equivalents) successively. The mixture is allowed to warm up to $0°$ C. after 10 minutes and stirred for 1 hour. The reaction mixture is washed with water, 2N-hydrochloric acid, water, aqueous 5% sodium hydrogen carbonate and water, dried over sodium sulfate and concentrated in vacuum. Obtained residue is purified by chromatography over silica gel containing 10% water to obtain 7β-(2-cyanopropionamido)-7α-methoxy-3-(1-methyl-5-tetrazolyl)-thiomethyl-1-dethia-1-oxa-3-cephem-4-carboxylic acid diphenylmethyl ester from the fraction eluted by a mixture of benzene and ethyl acetate (3:1). Yield: 88% as colorless foam.

IR: $\nu_{max}^{CHCl_3}$ 3420, 2250, 1785, 1720 cm$^{-1}$.

NMR: $\delta_{ppm}^{CDCl_3}$ 1.52d(7Hz)3H, 3.5brs1H, 3.13s3H, 3.71s3H, 4.08s2H, 4.58s2H, 5.02s1H, 6.88s1H.

(2) To an ice cooled solution of the product of the foregoing part (1) (57 g) in dichloromethane (12 parts by weight) are added anisole (1 part by weight) and trifluoroacetic acid (1 part by weight). After stirring for 1.5 hours, the reaction mixture is diluted with benzene (3 parts by weight) and concentrated in vacuum to leave the product which may separate as a pale yellow powder, 7β-(2-cyanopropionamido)-7α-methoxy-3-(1-methyl-5-tetrazolyl)thiomethyl-1-dethia-1-oxa-3-cephem-4-carboxylic acid on dilution with as hexane.

Yield: 98%. This product is the same with the product of the following part (3) of this Preparation 1.

IR: $\nu_{max}^{KBr}$ 3295, 2258, 1787, 1715 cm$^{-1}$.

UV: $\lambda_{max}^{CH_3OH}$ 273 nm ($\epsilon = 10500$).

(3) To a solution of the product of part (1) above (18 g) in anisole (2.8 parts by weight) cooled at $-30°$ C. are added aluminum chloride (3 equivalents) and anisole (7.4 parts by weight). After stirring at $-20°$ C. for 1 hour, the reaction mixture is diluted with ethyl acetate, washed with 2N-hydrochloric acid and aqueous saline, and extracted with aqueous sodium bicarbonate, washed with ethyl acetate, made pH 2 with hydrochloric acid, and extracted with ethyl acetate. The resulting solution is washed with saline and concentrated. The residue is triturated in hexane to give 7β-(2-cyanopropionamido-7α-methoxy-3-(1-methyl-5-tetrazolyl)thiomethyl-1-dethia-1-oxa-3-cephem-4-carboxylic acid as colorless powder.

Yield: 85%.

IR: $\nu_{max}^{KBr}$ 3295, 2258, 1787, 1715 cm$^{-1}$.

UV: $\lambda_{max}^{CH3OH}$ 273 nm ($\epsilon$=10,500).

NMR: $\delta_{ppm}^{CD3COCD3}$ (1.52d+1.53d)(7Hz)2H, 3.48s3H, 3.90q(7Hz) 1H, 3.95s3H, 4.31s2H, 4.65s2H, 5.09s1H, 8.42brs1H.

PREPARATION 2.

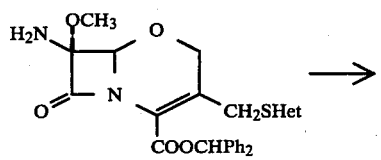

PREPARATION 3.

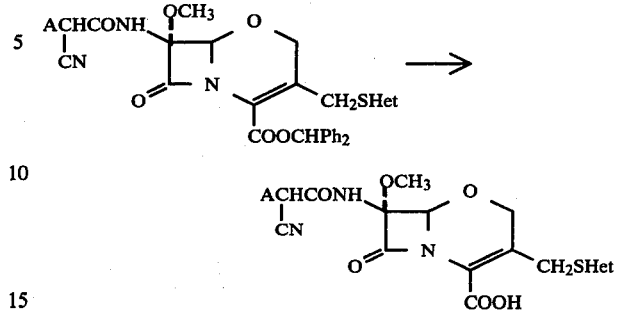

In a manner similar to that of Preparation 1 (2) and (3), free acids of the Table 2 can be prepared.

TABLE 1

| No. | A | Het | NMR: $\delta_{ppm}^{CDCl3}$ (Hz values are coupling constants) | Yield (%) |
|---|---|---|---|---|
| 1 | -C$_2$H$_5$ | Tetr. | 1.07t(7Hz)3H,1.98dq(7;7Hz)2H,3.48t(7Hz)1H,3.54s3H,3.75s3H,4.20s2H, 4.59s2H,5.02s1H,6.88s1H. | 86 |
| 2 | -n-C$_3$H$_7$ | Tetr. | 0.6-2.1m7H,3.34s3H,3.4brs1H,3.54s 3H,4.02s2H,4.41s2H,4.86s1H,6.73s1H. | 84 |
| 3 | -n-C$_4$H$_9$ | Tetr. | 0.6-2.2m9H,3.45s3H,3.5brs1H,3.62s 3H,4.12s2H,4.50s2H,4.97s1H,6.82s1H. | 97 |
| 4 | -C$_2$H$_5$ | Tdz | 1.10t(7Hz)3H,2.02dq(7,7Hz)2H,3.52t(7Hz)1H,3.55s3H,(4.35s + 4.45s)2H, 4.62s2H,5.05s1H,6.92s1H,8.92s1H. | 76 |
| 5 | -C$_2$H$_5$ | TdzMe | 1.07t(7Hz)3H,1.97dq(7;7Hz)2H,2.58s3H, 3.5brs1H,3.53s3H,(4.23s + 4.31s)2H,4.55s 2H,5.03s1H,6.92s1H. | 45 |

EXAMPLE 1.

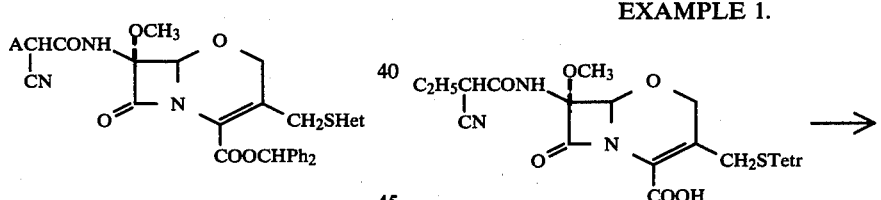

In a manner similar to that of Preparation 1(1), N-cyanoacylates of the Table 1 can be prepared.

TABLE 2

| No. | A | Het | NMR: $\delta_{ppm}^{CD3COCD3}$ (Hz values are coupling const.) | Yield (%) |
|---|---|---|---|---|
| 1 | —C$_2$H$_5$ | Tetr. | 1.07t(7Hz)3H,1.97dq(7;7Hz)2H,3.48s 3H,3.80t(7Hz)1H,3.96s3H,4.30s2H, 4.64s2H,5.08s1H,8.42brs1H. | quantitative[1] |
| 2 | -n-C$_3$H$_7$ | Tetr. | 0.7-2.2m7H,3.46s3H,3.82t(7Hz)1H, 3.94s3H,4.29s2H,4.63s2H,5.07sH, 8.40brs1H. | quantitative[1] |
| 3 | -n-C$_4$H$_9$ | Tetr. | 0.7-2.2m9H,3.48s3H,3.84t(7Hz)1H, 3.96s3H,4.31s2H,4.65s2H,5.09s1H, 8.43brs1H. | 96[1] |
| 4 | —C$_2$H$_5$ | Tdz | 1.10t(7Hz)3H,2.02dq(7;7Hz)2H,3.50s 3H,3.83t(7Hz)1H,(4.43s + 4.52s)2H, 4.66s2H,5.12s1H,9.37s1H. | 56[2] |
| 5 | —C$_2$H$_5$ | TdzMe | 1.08t(7Hz)3H,2.02dq(7;7Hz)2H,2.72s 3H,3.52s3H,3.85t(7Hz)1H,(4.39s + 4.45 s)2H,4.69s2H,5.13s1H. | 72[2] |

[1] Trifluoroacetic acid/anisole;
[2] aluminum chloride/anisole

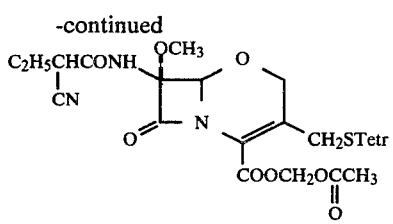

To a solution of 7β-(2-cyano-n-butyrylamino)-7α-methoxy-3-(1-methyl-5-tetrazolyl)thiomethyl-1-dethia-1-oxa-3-cephem-4-carboxylic acid (1.22 g) in acetone (5 parts by weight) is added a solution of sodium 2-ethylhexanoate in isopropanol (1 equeivalent) under ice cooling. After stirring for 10 minutes, the mixture is diluted with ether to separate sodium salt. This is collected by filtration, dried, dissolved in N,N-dimethylformamide (5 parts by weight), mixed with acetic acid bromomethyl ester (2 equivalents) and stirred at room temperature for 1 hour. The reaction mixture is diluted with ethyl acetate and water, shaken, and let stand to separate organic layer. This is washed with water, dried and concentrated in vacuum. The residue is chromatographed over a column of silica gel containing 10% water (25 parts by weight) to obtain 7β-(2-cyano-n-butyryl)amino-7α-methoxy-3-(1-methyl-5-tetrazolyl)-thiomethyl-1-dethia-1-oxa-3-cephem-4-carboxylic acid acetoxymethyl ester from the fraction eluted with a mixture of benzene and ethyl acetate (2:1). Yield: 50%.

IR: $\nu_{max}^{CHCl_3}$ 3400, 2220, 1795, 1720 cm$^{-1}$.

NMR: $\delta_{ppm}^{CDCl_3}$ 1.10t(7Hz)3H, 2.01dq(7;7Hz)2H; 2.15s3H, 3.5brs 1H, 3.54s3H, 3.95s3H, 4.30s2H, 4.67s2H, 5.08s1H, 5.82d (6Hz)1H, 5.94d(6Hz)1H, 7.61brs1H.

EXAMPLE 2

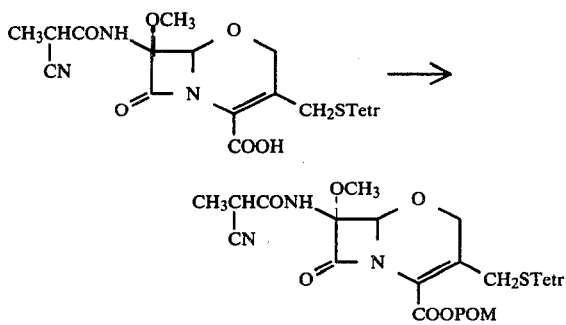

To an ice cold solution of 7β-(2-cyanopropionamido)-7α-methoxy-3-(1-methyl-5-tetrazolyl)thiomethyl-1-dethia-1-oxa-3-cephem-4-carboxylic acid sodium salt (42 g) in N,N-dimethylformamide (6.7 parts by weight) are added pivalic acid iodomethyl ester prepared by reacting sodium iodide (3.8 equivalents) and pivalic acid chloromethyl ester (3.8 equivalents) in acetone for 1 hour. After stirring for 90 minutes at room temperature, the reaction mixture is diluted with ethyl acetate, washed with aqueous sodium hydrogen sulfite and water, dried over magnesium sulfate and concentrated to dryness. The residue is washed with hexane and chromatographed over silica gel containing 10% water (25 parts by weight). The fraction eluted with a mixture of benzene and ethyl acetate (2:1) is lyophilized from benzene to give 7β-(2-cyanopropionamido)-7α-methoxy-3-(1-methyl-5-tetrazolyl)thiomethyl-1-dethia-1-oxa-3-cephem-4-carboxylic acid pivaloyloxymethyl ester as colorless powder. Yield: 52%.

IR: $\nu_{max}^{CHCl_3}$ 3420, 2250, 1793, 1753, 1720 cm$^{-1}$.

UV: $\lambda_{max}^{CH_3OH}$ 282 nm (ε: 9930).

NMR: $\delta_{ppm}^{CDCl_3}$ 1.23s9H, 1.59d(7Hz)3H, 3.53s3H, 3.60q(7Hz)1H, 4.25s2H, 4.63s2H, 5.04s1H, 5.81d(5Hz)1H, 5.99d(5Hz)1H, 7.25brs1H. 3.90s3H.

EXAMPLE 3

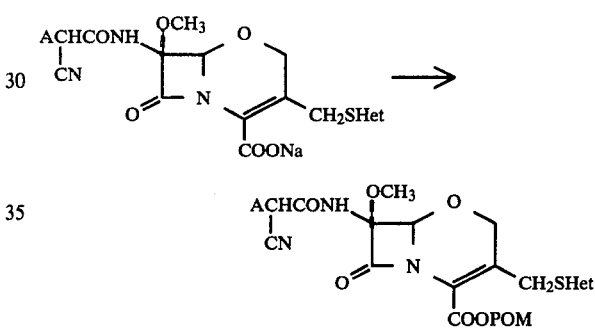

In a manner similar to that of Example 2, pivaloyloxymethyl esters of Table 3 are prepared.

In the reactions, 1 to 5 equivalents of sodium or potassium iodide and 1 to 6 equivalents of pivalic acid chloromethyl ester are reacted to give the iodomethyl ester at −10° C. to 40° C. for ½ to 3 hours.

EXAMPLE 4

TABLE 3

| No. | A | Het | NMR: $\delta_{ppm}^{CDCl_3}$ (Hz values are coupling constants) | Yield (%) |
|---|---|---|---|---|
| 1 | —C$_2$H$_5$ | Tetr | 1.11t(7Hz)3H,2.00dq(7;7Hz)2H,3.50t(7Hz)1H,3.53s3H,3.90s3H,4.26s2H,4.63s2H,5.04s2H,5.83d(5Hz)1H,5.98d(5Hz)1H,7.22brs1H,1.23s9H. | 58 |
| 2 | -n-C$_3$H$_7$ | Tetr | 0.97t(7Hz)3H,1.22s9H,1.3–2.2m4H,3.50t(7Hz)1H,3.53s3H,3.89s3H,4.26s2H,4.63s2H,5.03s1H,5.81d(5Hz)1H,5.98d(5Hz)1H,7.10brs1H. | 39 |
| 3 | -n-C$_4$H$_9$ | Tetr | 0.7–2.2m9H,1.23s9H,3.52t(7Hz)1H,3.53s3H,3.91s3H,4.27s2H,4.63s2H,5.04s1H,5.83d(5Hz)1H,6.00d(5Hz)1H,7.23brs1H. | 44 |
| 4 | —C$_2$H$_5$ | Tdz | 1.13t(7Hz)3H,1.24s9H,2.03dq(7;7Hz)2H,1.55s3H,1.55t(7Hz)1H,(4.37s + 4.52 s)2H,4.67s2H,5.09s1H,5.88d(5Hz)1H,6.05d(5Hz)1H,7.50brs1H,9.10s1H. | 66 |
| 5 | —C$_2$H$_5$ | TdzMe | 1.10t(7Hz)3H,1.21s9H,1.97dq(7;7Hz)2H,2.73s3H,3.54s3H,3.55t(7Hz)1H, | 70 |

TABLE 3-continued

| No. | A | Het | NMR: $\delta_{ppm}^{CDCl_3}$ (Hz values are coupling constants) | Yield (%) |
|---|---|---|---|---|
| | | | (4.29s + 4.44s)2H,4.63s2H,5.08s1H,5.88 d(5Hz)1H,6.02d(5Hz)1H,7.47s1H. | |

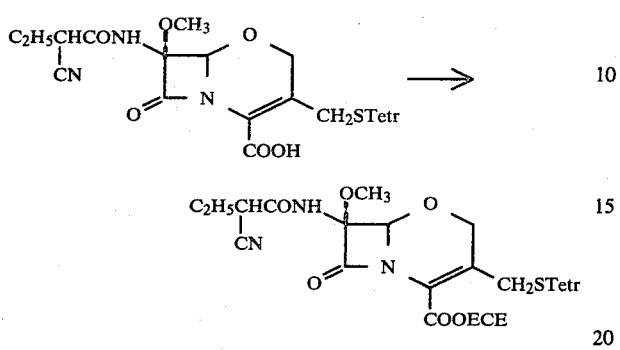

To a solution of 7β-(2-cyano-n-butyryl)amino-7α-methoxy-3-(1-methyl-5-tetrazolyl)thiomethyl-1-dethia-1-oxa-3-cephem-4-carboxylic acid (847 mg) in acetone (4.5 parts by weight) is added a solution of 2-ethylhexanoic acid sodium salt (1 equivalent) in isopropanol. After stirring at room temperature for 20 minutes, 1-iodoethyl ethoxyformate prepared by refluxing 1-chloroethyl ethoxyformate (2 equivalents) and sodium iodide (2 equivalents) in acetone for ½ hours and concentrating the solution is dissolved in a small amount of N,N-dimethylformamide and added to the above stated solution of the sodium salt. After stirring for 1 hour at room temperature, the mixture is diluted with ethyl acetate and water, shaken and allowed to stand still to separate organic layer. This is separated, washed with water, dried and concentrated. The residue is chromatographed over silica gel containing 10% water (20 parts by weight) to give 7β-(2-cyano-n-butyryl)amino-7α-methoxy-3-(1-methyl-5-tetrazolyl)thiomethyl-1-dethia-1-oxa-3-cephem-4-carboxylic acid 1-(ethoxycarbonyloxy)ethyl ester stereoisomer A (Yield: 11%) and stereoisomer B (14%) and mixture of the isomers A and B (Yield: 10%). These isomers are those due to isomerism at the asymmetric carbon in the ester part.

(Isomer A).
NMR: $\delta_{ppm}^{CDCl_3}$ 1.05t(7Hz)3H, 1.32t(7Hz)3H, 1.60d(6Hz)3H, 2.02dq(7;7Hz)2H, 3.53s3H, 3.6brs1H, 3.90s3H, 4.25q (7Hz)2H, 4.30s2H, 4.65s2H, 5.05s1H, 6.90q(6Hz)1H.

IR: $\nu_{max}^{CHCl_3}$ 3400, 2225, 1797, 1765, 1720 cm$^{-1}$.
(Isomer B)
NMR: $\delta_{ppm}^{CDCl_3}$ 1.05t(7Hz)3H, 1.32t(7Hz)3H, 1.60t(6Hz)3H, 2.01dq(7;7Hz)2H, 3.55s3H, 3.6brs1H, 3.90s3H, 4.27q(7Hz) 2H, 4.30s2H, 4.66s2H, 5.07s1H, 6.92q(6Hz)1H.

IR: $\nu_{max}^{CHCl_3}$ 3390, 2220, 1792, 1764, 1720, cm$^{-1}$.

EXAMPLE 5

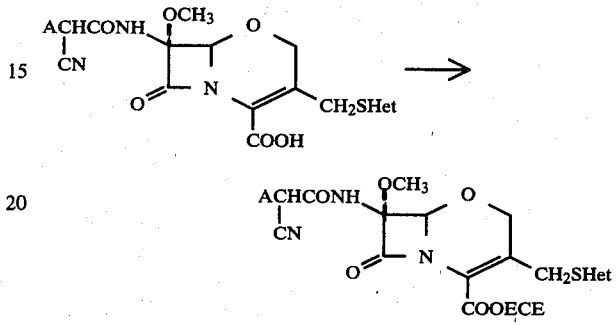

In a manner similar to that of Example 4, 1-(ethoxycarbonyloxy)ethyl esters of Table 4 are prepared.

In the synthesis are used chloroethyl ethoxyformate (1 to 3 equivalents) and sodium or potassium iodide (1 to 3 equivalents) at −10° C. to 40° C. for ½ to 3 hours.

TABLE 4

| No. | A | Het | NMR: $\delta_{ppm}^{CDCl_3}$ (Hz values are coupling constants) | Yield (%) |
|---|---|---|---|---|
| 1 | n-C$_3$H$_7$— (stereoisomer A) | Tetr | 0.95t(7Hz)3H,1.30t(7Hz)3H,1.61d(5Hz)3H,1.6–2.3m4H,3.53s3H,3.6brs1H,3.90s 3H,4.23q(7Hz)2H,4.28s2H,4.65s2H,5.05 s1H,6.85q(5Hz)1H,7.50brs1H. | 16 |
| | n-C$_3$H$_7$— (stereoisomer B) | Tetr | 0.95t(7Hz)3H,1.29t(7Hz)3H,1.62d(5Hz)3H,1.62–2.3m4H,3.53s3H,3.6brs1H,3.88s 3H,4.21q(7Hz)2H,4.28s2H,4.65s2H,5.08 s1H,6.90q(5Hz)1H,7.50brs1H. | 16 |
| 2 | C$_2$H$_5$— (stereoisomers) | Tdz | 1.07t(7Hz)3H,1.27(7Hz)3H,1.56d(5Hz)3H,2.06dq(7;7Hz)2H,3.39s3H,3.6brs1H,4.07q(7Hz)2H,4.23s2H,4.44s2H,4.85s1H,6.26q(5Hz)1H,7.15brs1H,8.621H. | 26 |

EXAMPLE 6

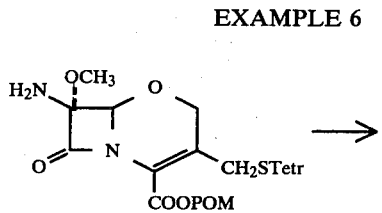

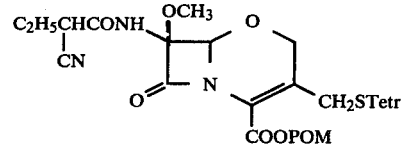

To a cooled solution of 7β-amino-7α-methoxy-3-(1-methyl-5-tetrazolyl)thiomethyl-1-dethia-1-oxa-3-cephem-4-carboxylic acid pivaloyloxymethyl ester (4.56 g) in dichloromethane (40 ml) at −20° C. are added 2-cyanobutyric acid (1.5 equivalents), pyridine (4.0 equivalents) and phosphorus oxychloride (1.5 equivalents). After stirring for 10 minutes at −20° C. and 1 hour at 0°

C., the reaction mixture is diluted with dichloromethane, washed with water, 2 N-hydrochloric acid, aqueous 5% sodium hydrogen carbonate and water, dried over magnesium sulfate and concentrated under reduced pressure. The residue is chromatographed over silica gel containing 10% water. By concentrating the fraction eluted with a mixture of benzene and ethyl acetate (2:1), one obtains 7β-(2-cyanobutyryl)-amino-7α-methoxy-3-(1-methyl-5-tetrazolyl)thiomethyl-1-dethia-1-oxa-3-cephem-4-carboxylic acid pivaloyloxymethylester. Yield: 87%. This product is identical with that of Example 3, No. 1.

Preparation of the starting 7β-amino-7α-methoxy-3-(1-methyl-5-tetrazolyl)thiomethyl-1-dethia-1-oxa-3-cephem-4-carboxylic acid pivaloyloxymethyl ester:

A solution of 7β-toluoylamino-7α-methoxy-3-(1-methyl-5-tetrazolyl)thiomethyl-1-dethia-1-oxa-3-cephem-4-carboxylic acid diphenylmethyl ester in a mixture of anisole (ca 10 parts by weight) and trifluoroacetic acid (ca. 5 parts by weight) is let stand for 1 hour and concentrated to leave the free acid (11.55 g). This is dissolved in ethyl acetate (7 parts by weight) and mixed with potassium 2-ethylhexanoate (1 equivalent) to separate the potassium salt. Yield: 88.7%.

The potassium salt (10 g) is dissolved in N,N-dimethylformamide (6 parts by weight), mixed with a solution of pivalic acid iodomethyl ester in N,N-dimethylformamide and allowed to react at room temperature for 2 hours. The reaction mixture is diluted with ethyl acetate and ice water, shaken and separate to obtain organic layer which is washed with water and purified by silica gel chromatography to give 7β-toluoylamino pivaloyloxymethyl ester. Yield: 49%.

NMR: $\delta_{ppm}^{CDCl_3}$ 1.23s9H, 2.38s3H, 3.57s3H, 3.88s3H, 4.28s2H, 4.62s2H, 5.17s1H, 5.88d(5 Hz)1H, 6.03d(5 Hz)1H, 6.97s1H, 7.22d(8 Hz)2H, 7.73d(8 Hz)2H.

The obtained 7β-toluoylamino pivaloyloxymethyl ester (5.63 g) is dissolved in dichloromethane (10 parts by weight), mixed successively with pyridine (2 equivalents) and phosphorus pentachloride (2 equivalents) and kept at room temperature for 2 hours. The reaction mixture is cooled at −30° C., mixed with methanol (25 parts by weight), stirred under ice cooling for 2 hours, cooled to −40° C., mixed with diethylamine (10 equivalents) and stirred at 1 hour under ice cooling. The reaction mixture is mixed with ethyl acetate and ice water, shaken and separate the organic layer. This is washed with water, dried and concentrated. The residue is purified by silica gel chromatography to give the objective 7β-amino-7α-methoxy-3-(1-methyl-5-tetrazolyl)thiomethyl-1-dethia-1-oxa-3-cephem-4-carboxylic acid pivaloyloxymethyl ester. Yield: 64%.

NMR: $\delta_{ppm}^{CDCl_3}$ 1.23s9H, 2.17brs2H, 3.48s3H, 3.92s3H, 4.30s2H, 4.70s2H, 4.87s1H, 5.87d(5 Hz)1H, 6.03d(5 Hz)1H.

EXAMPLE 7

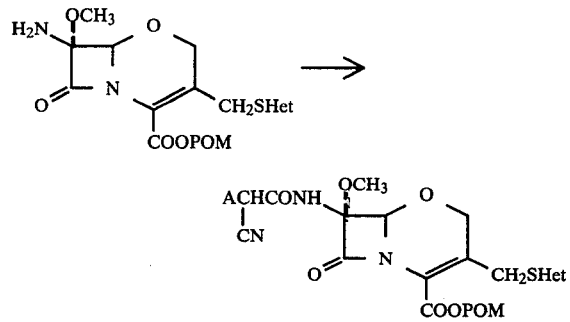

In a manner similar to that of Example 6, pivaloyloxymethyl esters of Table 5 are prepared.

TABLE 5

| No. | A | Het | NMR: $\delta_{ppm}^{CDCl_3}$ (Hz values are coupling constants) | Yield (%) |
|---|---|---|---|---|
| 1 | —CH₃ | Tetr | 1.23s9H,1.59d(7Hz)3H,3.53s3H,3.60q(7Hz)1H,3.90s3H,4.25s2H,4.63s2H,5.04s1H,5.81d(5Hz)1H,5.99d(5Hz)1H,7.25brs1H. | 52 |
| 2 | -n-C₃H₇ | Tetr | 0.97t(7Hz)3H,1.22s9H,1.3-2.2m4H,3.50t(7Hz)1H,3.53s3H,3.89s3H,4.26s2H,4.63s2H,5.03s1H,5.81d(5Hz)1H,5.98d(5Hz)1H,7.10brs1H. | 65 |
| 3 | -n-C₄H₉ | Tetr | 0.7–2.2m9H,1.23s9H,3.52(7H)1H,3.53s3H,3.91s3H,4.27s2H,4.63s2H,5.04s1H,5.83d(5Hz)1H,6.00d(5Hz)1H,7.23brs1H. | 49 |
| 4 | —C₂H₅— | Tdz | 1.13t(7Hz)3H,1.24s9H,2.03q(7;7Hz)2H,1.55s3H,1.55t(7Hz)1H,(4.37s + 4.52s)2H,4.67s2H,5.09s1H,5.88d(5Hz)1H,6.05d(5Hz)1H,7.50brs1H,9.10s1H. | 71 |
| 5 | —C₂H₅ | TdzMe | 1.10t(7Hz)3H,1.21s9H,1.97dq(7;7Hz)2H,2.73s3H,3.54s3H,3.55t(7Hz)1H,(4.29s + 4.44s)2H,4.63s2H,5.08s1H,5.88d(5Hz)1H,6.02d(5Hz)1H,7.47s1H. | 75 |

EXAMPLE 8

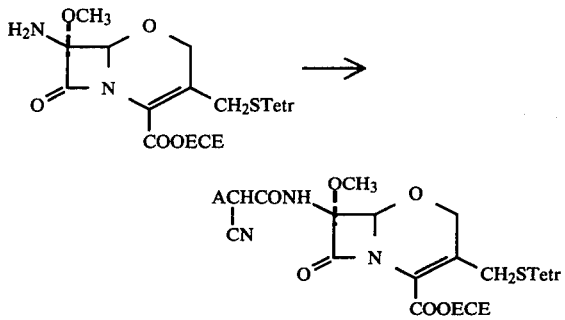

To a solution of 7β-amino-7α-methoxy-3-(1-methyl-5-tetrazolyl)thiomethyl-1-dethia-1-oxa-3-cephem-4-carboxylic acid 1-(ethoxycarbonyloxy)ethyl ester (6.21 g)

in dichloromethane (40 ml) at −20° C. are added α-cyanobutyric acid (1.2 equivalents), pyridine (3.0 equivalents) and phosphorus oxychloride (1.2 equivalents). After stirring at 0° C. for 1 hour, the mixture is diluted with dichloromethane, washed with water, 2 N-hydrochloric acid and water, dried over sodium sulfate and concentrated. The residue is chromatographed over silica gel containing 10% water. Concentration of fractions eluted with a mixture of benzene and ethyl acetate (2:1) gives 7β-(2-cyano-n-buryryl)amino-7α-methoxy-3-(1-methyl-5-tetrazolyl)thiomethyl-1-dethia-1-oxa-3-cephem-4-carboxylic acid 1-(ethoxycarbonyloxy)ethyl ester. Yield: 72%. This product is the same as that of Example 4.

The starting 7β-amino-7α-methoxy-3-(1-methyl-5-tetrazolyl)thiomethyl-1-dethia-1-oxa-3-cephem-4-carboxylic acid 1-(ethoxycarbonyloxy)ethyl ester can be prepared by the method similar to that of Example 6 for making the corresponding pivaloyloxymethyl ester.

In a manner similar to above, additional 1-ethoxycarbonyloxyethyl esters may be prepared. In representative cases, there are used 1.1 to 1.5 equivalents of the acylating reagent, 2 to 5 equivalents of pyridine and the same molar ratio of phosphorus oxychloride with that of the acylating reagent, all as compared with the amount of the amine at 15° C. to −20° C. for 1 hour.

EXAMPLE 9

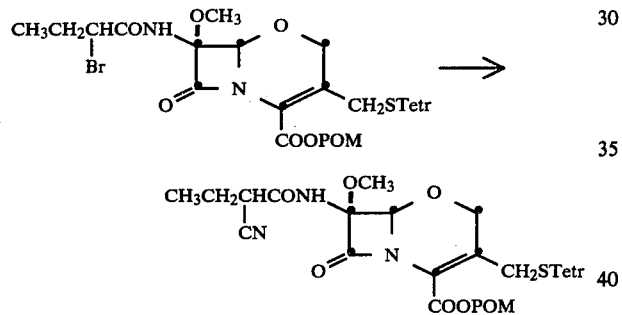

To a solution of 7β-(2-bromobutanamido)-7α-methoxy-3-(1-methyl-5-tetrazolyl)thiomethyl-1-dethia-1-oxa-3-cephem-4-carboxylic acid pivaloyloxymethyl ester (1.21 g) in dichloromethane (5 ml) is added potassium cyanide (2 equivalents) and aqueous tetra-N-butylammonium bromide (0.1 equivalent). The mixture is stirred vigorously at room temperature for 3 hours. The organic layer is separated, washed with water, dried and concentrated in vacuum. The residue is chromatographed over silica gel containing 10% water. From the fraction eluted with a mixture of benzene and ethyl acetate (2:1), man obtains 7β-(2-cyanobutyrylamino)-7α-methoxy-3-(1-methyl-5-tetrazolyl)thiomethyl-1-dethia-1-oxa-3-cephem-4-carboxylic acid pivaloyloxymethyl ester. Yield: 43%.

By the method similar to above, the products of Example 2 to 4 are prepared.

Preparation of the starting 7β-(2-bromobutyrylamino)-7α-methoxy-3-(1-methyl-5-tetrazolyl)thiomethyl-1-dethia-1-oxa-3-cephem-4-carboxylic acid pivaloyloxymethyl ester:

(1) Acylation of 7β-amino-7α-methoxy-3-(1-methyl-5-tetrazolyl)thiomethyl-1-dethia-1-oxa-3-cephem-4-carboxylic acid diphenylmethyl ester with α-bromobutyric acid (1.1 equivalent), phosphorus oxychloride (1.1 equivalent) and pyridine (4 equivalents) at 0° C.

NMR: $\delta_{ppm}^{CDCl_3}$ 1.05t(7 Hz)3H, 2.10dq(7 Hz)2H, 3.57s3H, 3.77s3H, 4.27s2H, 4.32t(7 Hz)1H, 4.63s2H, 5.07s1H, 6.90s1H.

(2) Removal of diphenylmethyl group is carried out by treating this acylate ester with aluminum chloride (3 equivalents) in anisole at 0° C. for 20 minutes gives the corresponding free carboxylic acid, mp. 85° to 87° C. Yield: 72%.

NMR: $\delta_{ppm}^{CD_3OD}$ 1.00t(7 Hz)3H, 2.02dq(7 Hz)2H, 3.55s3H, 3.98s3H, 4.25s2H, 4.33t(7 Hz)1H, 4.60s2H, 5.07s1H.

IR: $\nu_{max}^{Nujol}$ 3200, 1775, 1713 cm$^{-1}$.

(3) The free acid is treated with sodium 2-ethylhexanoate to obtain the solid sodium salt. The salt is then treated with iodomethyl pivalate in dimethylformamide to give objective bromobutanamido ester, m.p. 50° to 53° C. Yield: 76%.

NMR: $\delta_{ppm}^{CDCl_3}$ 1.05t(7 Hz)3H, 1.25s9H, 2.10dq(7 Hz)2H, 3.57s 3H, 4.32t(7 Hz)1H, 4.66s2H, 5.10s1H, 5.88d(5 Hz)1H, 6.01d((5 Hz)1H, 7.23brs1H, 3.93s3H.

IR: $\nu_{max}^{Nujol}$ 3290, 1787, 1753, 1703 cm$^{-1}$.

EXAMPLE 10

| | |
|---|---|
| 7β-(2-Cyanobutanamido)-7α-methoxy-3-(1,3,4-thiadiazol-5-yl)thiomethyl-1-dethia-1-oxa-3-cephem-4-carboxylic acid sodium salt: | 10 g |
| Sterile water for injection | 40 g |

Above two materials are mixed together to make a solution. Each 5 g of the solution is distributed into 10 vials, cooled to solidify and lyophilized. Two vials per day are given to a subject intravenously or by drip for treating or preventing infections caused by sensitive bacteria.

EXAMPLE 11

| | |
|---|---|
| 7β-(2-Cyanobutanamido)-7α-methoxy-3-(1-methyl-5-tetrazolyl)thiomethyl-1-dethia-1-oxa-3-cephem-4-carboxylic acid 1-ethoxycarbonyloxyethyl ester | 250 g |
| Corn starch | 150 g |
| Magnesium stearate | 5 g |

Above three materials are mixed, filled in hard capsules (500 mg volume) to make 1000 capsules. This is given to a patient suffering from an infection caused by sensitive gram-negative bacteria at a dose of 3 to 6 capsules in 3 times per day.

EXAMPLE 12

| | |
|---|---|
| 7β-(2-Cyanopropionamido)-7α-methoxy-3-(1-methyl-5-tetrazolyl)thiomethyl-1-dethia-1-oxa-3-cephem-4-carboxylic acid pivaloyloxymethyl ester | 250 g |
| Magnesium stearate | 2 g |
| Corn starch | 140 g |
| Sodium carboxymethyl starch | 5 g |

The antibacterial constituent and magnesium stearate are mixed and pressed to make tablet slug. The 16 to 20 mesh portion is collected, blended with sodium carboxymethyl starch and corn starch. The mixture is compressed to make tablets. They are subjected to film coating to produce 1000 pieces of 400 mg tablets. The pills are given orally to a patient suffering from an infection caused by gram positive bacteria sensitive to the antibacterial at a dose of 4 to 8 tablets in 4 times per day.

EXAMPLE 13

| | |
|---|---|
| 7β-(2-Cyanobutanamido)-7α-methoxy-3-(1-methyl-5-tetrazolyl)thiomethyl-1-dethia-1-oxa-3-cephem-4-carboxylic acid pivaloyloxymethyl ester as powder of less than 100 mesh | 10 g |
| Triglyceride of higher fatty acid | 80 g |
| Polyoxyethylene oleyl alcohol ether | 10 g |

To a fuzed triglyceride at 40° C. are added other two materials, dispersed uniformly by gentle stirring and then cooled to solidifying point. This is distributed to an apparatus and cooled to make 100 suppositories. This is given to a child suffering from upper respiratory tract infection at a dose of two suppositories per day.

Experiment 1. (Recovery in urine)

To each group consisting of 5 mice weighing 25 g is administered orally a suspension of the Compound (1) below in 5% acacia solution using a tube to stomach. Urine sample during 2 hours thereafter and urine contained in the bladder are combined, antibacterial activity against *Escherichia coli* 7437 determined by microbiological assay using zone culture method, and the antibacterial activity in urine, calculated as the content of the corresponding mole ratio of carboxylic acid (2). Urinary recovery is represented by mole ratio of the obtained activity in urine sample to administered ester (1) in percent. The results are listed on Table A.

TABLE A

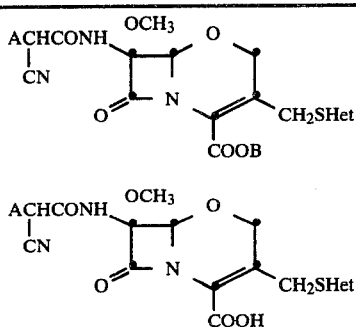

| No. | A | B | Het | Recovery in urine (2 hr) (%) |
|---|---|---|---|---|
| 1 | CH$_3$— | POM | Tetr | 52.1 |
| 2 | C$_2$H$_5$— | POM | Tetr | 15.2 |
| 3 | n-C$_3$H$_7$— | POM | Tetr | 7.7* |
| 4 | n-C$_4$H$_9$— | POM | Tetr | 1.2* |
| 5 | C$_2$H$_5$— | ECE | Tetr | 14.9 |
| 6 | C$_2$H$_5$— | ECE | Tetr | 14.7 |
| 7 | n-C$_3$H$_7$— | ECE | Tetr | 5.3 |
| 8 | n-C$_3$H$_7$— | ECE | Tetr | 6.5 |
| 9 | C$_2$H$_5$— | POM | Tdz | 22.9 |
| 10 | C$_2$H$_5$— | ECE | Tdz | 22.0 |
| 11 | C$_2$H$_5$— | POM | TdzMe | 15.4 |

*Recovery in 4 hours. No. 5 and No. 6 as well as No. 7 and No. 8 are sets of stereoisomers in terms of ester part. No. 5 and No. 7 are more polar and No. 6 and No. 8 are less polar isomers.

EXPERIMENT 2 (PROTECTION TEST)

To each group consisting of 5 to 10 mice is challenged 2 to 3×10$^5$ *Escherichia coli* EC-14 in 5% mucin intraperitoneally. After 1 hour and 5 hours, a suspension of the ester (1) in the foregoing experiment in 5% acacia solution is administered enterally using a tube into stomach. From the survival rate after 7 days, ED$_{50}$ of the drug is calculated, and the value in mg/kg is interpreted as the corresponding carboxylic acid.

For using as control, it is necessary to use the effect of the corresponding carboxylic acid. However, the acid is hardly absorbed orally only up to 3 to 6% of subcutaneous injection and does not allow the estimation. Then instead, the ED$_{50}$ value of the corresponding carboxylic acid (2) on subcutaneous injection is assayed and this is used to evaluate the enteral absorption of the ester (1).

The control value of ED$_{50}$ for the carboxylic acid (2) is estimated as follows: To each group consisting of 5 to 10 mice challenged by *Escherichia coli* EC-14 intraperitoneally as in the case of oral experiment above is injected a solution of the carboxylic acid (2) in 0.7% aqueous sodium hydrogen carbonate subcutaneously after 1 and 5 hours after the challenge. The ED$_{50}$ value is calculated from the survival rate from 7 days and expressed in mg/kg value. The results are listed in Table B.

TABLE B

| No. | A | B* | Het | ED$_{50}$ of Ester (1) p.o. | ED$_{50}$ of Acid (2) subc. |
|---|---|---|---|---|---|
| 1 | CH$_3$— | POM | Tetr | 5.32 | 1.68 |
| 2 | C$_2$H$_5$— | POM | Tetr | 1.39 | 0.47 |
| 3 | n-C$_3$H$_7$— | POM | Tetr | 5.32 | 0.60 |
| 4 | n-C$_4$H$_9$— | POM | Tetr | 29.8 | 3.18 |
| 5 | C$_2$H$_5$— | ECE | Tetr | 2.22 | 0.45 |
| 6 | C$_2$H$_5$— | ECE | Tetr | 2.35 | 0.45 |
| 7 | n-C$_3$H$_7$— | ECE | Tetr | 4.70 | 0.60 |
| 8 | n-C$_3$H$_7$— | ECE | Tetr | 2.82 | 0.60 |
| 9 | C$_2$H$_5$— | POM | Tdz | 6.50 | 0.77 |
| 10 | C$_2$H$_5$— | ECE | Tdz | 3.23 | 0.77 |
| 11 | C$_2$H$_5$— | POM | TdzMe | 3.70 | 0.87 |

*No. 5 and No. 6 as well as No. 7 and No. 8 are sets of stereoisomers in terms of ester part. No. 5 and No. 7 are more polar and No. 6 and No. 8 are less polar isomers.

Additional Examples 1 to 14

According to a manner similar to that of the foregoing Examples, novel compounds of the Table 6 can be prepared.

The reactions and yields are as follows:

| Compound No. | Reaction | Yield |
|---|---|---|
| 1 | amidation | 76% |
| 2 | deesterification | 69% |
| 3 | amidation | 91% |
| 4 | deesterification | 98% |
| 5 | salt formation | 98% |
| 6 | esterification | 68% |
| 7 | esterification | 75% |
| 8 | amidation | quantitative |
| 9 | deesterification | quantitative |
| 10 | esterification | 32% |
| 11 | esterification | 55% |
| 12 | esterification | 27% |
| 13 | esterification | 25% |
| 14 | salt formation | 94% |

Similarly prepared 7β-(2-cyanopropionamido)-7α-methoxy-3-(1-methyl-5-tetrazolyl)thiomethyl-1-dethia-1-oxa-3-cephem-4-carboxylic acid sodium salt prepared by the salt formation has the following physical constants.

IR: $\nu_{max}^{KBr}$ 3400, 2230, 1770, 1703, 1603 cm$^{-1}$.

NMR: $\delta_{ppm}^{D2O}$ 1.61s3H, 3.54s3H, 4.02s3H, 4.17s2H, 4.57s2H, 5.16s1H.

TABLE 6

Structure: C₂H₅CHCONH- (with CN substituent) attached to a cephem nucleus with OCH₃, O, N, COOB, CH₂S-linked to a triazole bearing R substituent.

| No. | B | R | IR: $\nu_{max}^{CHCl_3}$ cm$^{-1}$ | NMR: $\delta_{ppm}^{CDCl_3}$ |
|---|---|---|---|---|
| 1 | —CHPh₂ | —CH₂COOCHPh₂ | 2230, 1785, 1750, 1714. | 1.08t(7Hz)3H, 1.92dq(7;7Hz)2H, 3.42t(7Hz)1H, 3.55s3H, 4.13s2H, 4.52s2H, 5.00s1H, 5.00s2H, 6.87s 2H. |
| 2 | —H | —CH₂COOH | 3500–3100, 2240, 1780, 1708(KBr) | 1.07t(7Hz)3H, 1.93dq(7;7Hz)2H, 3.47s3H, 3.81t(7Hz)1H, 4.38s2H, 4.65s2H, 5.12s1H, 5.32s2H. |
| 3 | —CHPh₂ | —CH₂CH₂SCH₃ | 3400, 2240, 1790, 1720, 1630. | 2.88t(7Hz)2H, 3.50t(8Hz)1H, 3.58 s3H, 4.28s2H, 4.32t(7Hz)2H, 4.80s 2H, 5.07s1H, 6.90s1H, 7.1–7.7m. |
| 4 | —H | —CH₂CH₂SCH₃ | 3490, 3275, 2495, 2250, 1784, 1705, 1635(Nujol). | 1.10t(8Hz)3H, 2.03m2H, 2.12s3H, 3.05t(6Hz)2H, 3.52s3H, 3.83t(8Hz) 1H, 4.37s2H, 4.57t(6Hz)2H, 4.68s 2H, 5.10s1H, 7.87brs1H(CD₃COCD₃) UV: $\lambda_{max}^{CH3OH}$ 229 ($\epsilon$ = 8100); 275nm ($\epsilon$ = 10200). |
| 5 | —Na | —CH₂CH₂SCH₃ | 3515, 3272, 3215, 2265, 1770, 1703, 1613(Nujol). | UV: $\lambda_{max}^{CH3OH}$ 230nm ($\epsilon$ = 9700); 272nm ($\epsilon$ = 11000). |
| 6 | —CH₂OCOC(CH₃)₃ | —CH₂CH₂SCH₃ | 1775, 1735, 1730. | 1.12t(7Hz)3H, 1.23s9H, 2.03m2H, 2.12s3H, 2.97t(7Hz)2H, 3.53t (7Hz)1H, 3.57s3H, 4.32s2H, 4.43 t(7Hz)2H, 4.65s2H, 5.07s1H, 5.85 ABq, A-part(6Hz)1H, 6.00ABq B-part(6Hz)1H. |
| 7. | —CH₂OC(=O)— (with CH₃ on ring) | —CH₃ | 3400, 1785, 1730, 1710. | 1.10t(7Hz)3H, 1.27s3H, 1.5–2.3 m10H, 3.55t(7Hz)1H, 3.57s3H, 3.93s3H, 4.28s2H, 4.65s2H, 5.07 s1H, (5.88d + 5.97d)ABq(7Hz)2H. |
| 8 | —CHPh₂ | —CH₂CH₂N(CH₃)₂ | 3400, 2242, 1785, 1733. | 1.10t(7Hz)3H, 2.00dq(7;7Hz)2H, 2.18s6H, 2.67t(6Hz)H, 3.43t (7Hz)1H, 3.55s3H, 4.17t(6Hz)2H, 4.21s2H, 4.59s2H, 5.02s1H, 6.91 s1H. |
| 9 | —H | —CH₂CH₂N(CH₃)₂ CF₃COOH | 3400, 2600, 2250, 1887, 1670–1710. | 1.13t(7Hz)3H, 1.98dq(7;7Hz)2H, 3.09s6H, 3.50s3H, 3.9brs1H, 3.87t(6Hz)2H, 4.27s2H, 4.63s2H, 4.91t(6Hz)2H, 5.06s1H(CD₃COCD₃). |
| 10 | —POM | —CH₂CH₂N(CH₃)₃ | 3400, 2250, 1790, 1761, 1733. | 1.17t(7Hz)3H, 1.23s9H, 2.00dq (7;7Hz)2H, 2.23s6H, 2.73t(7Hz)2H 3.50t(7Hz)1H, 3.53s3H, 4.27s2H, 4.28t(7Hz)2H, 4.63s2H, 5.05s1H, (5.85d + 6.00d)ABq(5Hz)2H, 7.1 brs1H. |
| 11 | —CH₂OCOOC₄H₉—t | —CH₃ | 3400, 2230, 1785, 1760, 1710. | 1.11t(8Hz)3H, 1.50s9H, 2.00dq (8;8Hz)2H, 3.60s3H, 3.61t(8Hz)1H 3.97s3H, 4.32s2H, 4.68s2H, 5.09 s1H, (5.82d + 5.95d)ABq(6Hz)2H, 7.5brs1H. |
| 12 | —CHOCOOC₄H₉—t (with CH₃) (polar isomer) | —CH₃ | 3400, 2230, 1785, 1755, 1708. | 1.12t(8Hz)3H, 1.52s9H, 1.58d (6Hz)3H, 2.00dq(8;8Hz)2H, 3.50t (8Hz)1H, 3.58s3H, 3.95s3H, 4.30 s2H, 4.65s2H, 5.07s1H, 6.90q (6Hz)1H, 7.1brs1H. |
| 13 | —CHOCOOC₄H₉—t (with CH₃) (nonpolar isomer) | —CH₃ | 3400, 2225, 1782, 1750, 1710. | 1.12t(8Hz)3H, 1.52s9H, 1.59d (8Hz)3H, 2.01dq(8;8Hz)2H, 3.52t (8Hz)1H, 3.58s3H, 3.95s3H, 4.30s 2H, 4.67s2H, 5.05s1H, 6.88q(6Hz) 1H, 7.2brs1H. |
| 14 | —Na | —CH₃ | 3420, 2250, 1770, 1700, 1612(KBr) | 1.09t(7Hz)3H, 2.02q(7Hz)2H, 3.54 s3H, 4.02s3H, (4.07d + 4.20d)Abq (14Hz)2H, 4.55s2H, 5.16s1H(D₂O). |

What we claim is:

1. A 7β-(2-cyanoaliphatic acyl)amino-7α-methoxy-3-heterocyclic thiomethyl-1-dethia-1-oxa-3-cephem-4-carboxylic acid compound represented by the following formula:

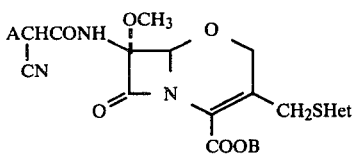

wherein

A is $C_1$ to $C_8$ alkyl, $C_2$ to $C_8$ alkenyl or $C_2$ to $C_8$ alkynyl;

B is (1) a hydrogen atom, (2) a salt forming light metal atom selected from the group of lithium, sodium, potassium, magnesium, calcium and aluminum, (3) $C_1$ to $C_8$-alkanoyloxy- $C_1$ to $C_5$-alkyl, (4) $C_1$ to $C_5$-alkoxycarbonyloxy-$C_1$ to $C_4$-alkyl or (5) phthalidyl; and Het is a heterocyclic radical selected from the group of triazolyl, tetrazolyl, thiadiazolyl, oxadiazolyl, thiazolyl, oxazolyl, isoxazolyl, triazinyl, pyridyl and pyrimidyl, said heterocyclic radicals being unsubstituted or substituted by (a) alkyl, (b) haloalkyl, (c) hydroxyalkyl, (d) alkoxyalkyl, (e) carboxylalkyl, (f) BOOC-alkyl wherein B is as defined above, (g) carbamoylalkyl, (h) N-alkylcarbamoylalkyl, (i) dialkylaminoalkyl, (j) sulfamoylalkyl, (k) alkylthioalkyl, all of the above said groups (a) to (k) containing 1 to 6 carbon atoms, (l) hydroxy, (m) oxo or (n) halogen.

2. A compound as claimed in claim 1 wherein A is $C_1$ to $C_4$-alkyl.

3. A compound as claimed in claim 1 wherein A is $C_3$ to $C_4$-alkenyl or $C_3$ to $C_4$-alkynyl.

4. A compound as claimed in claim 2 wherein A is methyl, ethyl, propyl, isopropyl, butyl, isobutyl or pentyl.

5. A compound as claimed in claim 3 wherein A is vinyl, allyl, butenyl or propargyl.

6. A compound as claimed in claim 1 wherein B is hydrogen.

7. A compound as claimed in claim 1 wherein B is lithium, sodium, potassium, magnesium, calcium or aluminum.

8. A compound as claimed in claim 1 wherein B is acetoxymethyl, pivaloyloxymethyl, 1-methylcyclopentylcarbonyloxymethyl, methoxycarbonyloxymethyl, methoxycarbonyloxyethyl, ethoxycarbonyloxymethyl, ethoxycarbonyloxyethyl, ethoxycarbonyloxyethyl, butoxycarbonyloxymethyl, butoxycarbonyloxyethyl, isopropyloxycarbonyloxyethyl or phthalidyl.

9. A compound as claimed in claim 1 wherein Het is substituted by methyl, carboxymethyl, BOOC-$CH_2$—dimethylaminoethyl, methylthioethyl, or hydroxyethyl.

10. A compound as claimed in claim 1 that has methyl, ethyl, propyl or butyl as A, hydrogen or sodium as B and 1-methyl-5-tetrazolyl as Het.

11. A compound as claimed in claim 1 that has methyl, ethyl, propyl or butyl as A, pivaloyloxymethyl as B and 1-methyl-5-tetrazolyl as Het.

12. A compound as claimed in claim 1 that has methyl, ethyl or propyl as A, ethoxycarbonyloxyethyl as B and 1-methyl-5-tetrazolyl as Het.

13. A compound as claimed in claim 1 that has ethyl as A, hydrogen, sodium, or pivaloyloxymethyl as B and 1-(methylthioethyl-5-tetrazolyl as Het.

14. A compound as claimed in claim 1 that has ethyl as A, hydrogen, sodium or pivaloyloxymethyl as B and 1-(2-dimethylaminoethyl)-5-tetrazolyl as Het.

15. A compound as claimed in claim 1 that has ethyl as A, t-butoxycarbonyloxymethyl, t-butoxycarbonyloxyethyl, hydrogen or sodium as B and 1-methyl-5-tetrazolyl as Het.

16. A compound as claimed in claim 1 that has ethyl as A, hydrogen, sodium, pivaloyloxymethyl or ethoxycarbonyloxyethyl as B, and 1,3,4-thiadiazol-2-yl as Het.

17. A compound as claimed in claim 1 that has ethyl as A, hydrogen, sodium, or pivaloyloxymethyl as B and 2-methyl-1,3,4-thiadiazol-5-yl as Het.

18. An antibacterial preparation containing an antibacterially effective amount of a compound as defined in claim 1 and a pharmaceutical carrier.

19. An antibacterial preparation according to claim 18, that is an enteral preparation containing a biochemically acceptable ester compound as defined in claim 1 and a pharmaceutical carrier.

20. A method for treating or preventing a bacterial infection of human or warm-blooded animal caused by bacteria sensitive to a compound as defined in claim 1 which comprises administering an antibacterially effective amount of the compound to the subject by enteral or parenteral route.

* * * * *